United States Patent
Tremel

(10) Patent No.: US 10,336,674 B2
(45) Date of Patent: Jul. 2, 2019

(54) PROCESS AND SYSTEM FOR CHEMICAL SYNTHESIS

(71) Applicant: Siemens Aktiengesellschaft, Munich (DE)

(72) Inventor: Alexander Tremel, Möhrendorf (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 0 days.

(21) Appl. No.: 15/749,618

(22) PCT Filed: Jul. 27, 2016

(86) PCT No.: PCT/EP2016/067861
§ 371 (c)(1),
(2) Date: Feb. 1, 2018

(87) PCT Pub. No.: WO2017/021245
PCT Pub. Date: Feb. 9, 2017

(65) Prior Publication Data
US 2018/0221841 A1    Aug. 9, 2018

(30) Foreign Application Priority Data
Aug. 5, 2015    (DE) .................. 10 2015 214 943

(51) Int. Cl.
*C07C 29/151*    (2006.01)
*B01J 8/00*    (2006.01)
*C07C 31/04*    (2006.01)

(52) U.S. Cl.
CPC ......... *C07C 29/1512* (2013.01); *B01J 8/0005* (2013.01); *C07C 31/04* (2013.01); *B01J 2208/00539* (2013.01)

(58) Field of Classification Search
CPC ... C07C 29/15; C07C 29/151; C07C 29/1512; C07C 31/04; B01J 8/0005; B01J 2208/00539
See application file for complete search history.

(56) References Cited

U.S. PATENT DOCUMENTS 3,649,208 A * 3/1972 Hornschuch .............. B01J 3/04
417/377
4,239,693 A * 12/1980 McCallister ........ C07C 29/1518
518/728
(Continued)

FOREIGN PATENT DOCUMENTS

DE    1667322 A1    6/1971    ............... C01C 1/04
DE    102004059315    *    6/2006    ............... B01J 3/00
(Continued)

OTHER PUBLICATIONS

Tidona, Bruno et al., "CO₂Hydrogenation to Methanol at Pressures up to 950 Bar," The Journal of Supercritical Fluids, vol. 78, pp. 70-77, Mar. 27, 2013.
(Continued)

*Primary Examiner* — Yate' K Cutliff
(74) *Attorney, Agent, or Firm* — Slayden Grubert Beard PLLC

(57) ABSTRACT

The present disclosure relates to chemical synthesis. Various embodiments of the teachings thereof may include the synthesis of methanol, generated from hydrogen and a carbonaceous gas. For example, a method may include: compressing gaseous starting materials to an operating pressure of at least 200 bar; supplying the starting materials to a synthesis reactor; removing a product mixture from the synthesis reactor in a liquid state; withdrawing mechanical energy from the product mixture by reducing a pressure of
(Continued)

the product mixture; and using the mechanical energy to compress the gaseous starting materials.

9 Claims, 2 Drawing Sheets

(56) References Cited

U.S. PATENT DOCUMENTS

| | | | |
|---|---|---|---|
| 4,321,234 A | 3/1982 | Ohsaki et al. | ............ 422/200 |
| 2004/0198847 A1 | 10/2004 | Hojlund Nielsen et al. | ............ 518/726 |

FOREIGN PATENT DOCUMENTS

| | | | | |
|---|---|---|---|---|
| DE | 102004059315 A1 | 6/2006 | ............ | B01J 3/00 |
| DE | 102012204985 A1 | 10/2013 | ............ | C07C 1/04 |
| EP | 2301886 A1 | 3/2011 | ............ | C01B 3/02 |
| GB | 1183304 A | 3/1970 | ............ | C01C 1/04 |
| GB | 2082574 * | 3/1982 | ............ | C07C 29/15 |
| WO | 2017/021245 A1 | 2/1917 | ............ | B01J 8/00 |
| WO | 2007/003909 A1 | 1/2007 | ............ | C07C 29/151 |

OTHER PUBLICATIONS

German Office Action, Application No. 102015214943.9, 8 pages, dated Apr. 8, 2016.
International Search Report and Written Opinion, Application No. PCT/EP2016/067861, 12 pages, dated Oct. 26, 2016.
European Office Action, Application No. 16745693.8, 6 pages, dated Oct. 31, 2018.

* cited by examiner

PROCESS AND SYSTEM FOR CHEMICAL SYNTHESIS

CROSS-REFERENCE TO RELATED APPLICATIONS

This application is a U.S. National Stage Application of International Application No. PCT/EP2016/067861 filed Jul. 27, 2016, which designates the United States of America, and claims priority to DE Application No. 10 2015 214 943.9 filed Aug. 5, 2015, the contents of which are hereby incorporated by reference in their entirety.

TECHNICAL FIELD

The present disclosure relates to chemical synthesis. Various embodiments of the teachings thereof may include the synthesis of methanol, wherein methanol is generated in a synthesis reactor out of the starting materials of hydrogen and a carbonaceous gas.

BACKGROUND

The increasing generation of electricity from renewable, fluctuating sources of energy (solar and wind energy) may occasion periods in which the rate of electricity generation exceeds the contemporaneous rate of electricity consumption. The then inexpensively available surplus electricity can be used in such periods to produce, for example, hydrogen via a hydrogen electrolysis. Adding a carbon source, for example carbon dioxide CO2, will then also make possible the production of synthesis products such as methanol. The chemical reaction used for this is as follows:

$$CO_2 + 3\ H_2 \rightarrow CH_3OH + H_2O \quad \text{(reaction formula 1)}$$

The chemical equilibrium in this reaction is largely on the left-hand side, resulting under customary reaction conditions of 200 to 300° C. and 30 to 80 bar pressure in but a very low degree of conversion for the starting materials passing through the reactor. Increasing the reaction pressure, however, causes the reaction equilibrium to shift to the right-hand side, as known from Tidona, B. et al. (2013), "CO2 hydrogenation to methanol at pressures up to 950 bar", Journal of Supercritical Fluids 78, pp. 70-77. Even just a pressure of about 300 bar will cause a nearly complete displacement of the reaction equilibrium onto the side of the products, methanol and water. High conversions are thus achieved for a single pass through the synthesis reactor. Being in liquid form, the reaction products of methanol and water are withdrawable from the equilibrium-limited methanol synthesis reaction in a continuous manner. The process described is disadvantageous because the high energy requirements for compressing the hydrogen and carbon dioxide starting materials to the desired pressure make commercial practice distinctly unattractive. The same problem also presents with other chemical types of synthesis processes where liquid products are formed under high pressure.

SUMMARY

The teachings of the present disclosure may enable a synthesis process and apparatus for said synthesis which reduce the disadvantage of the extant processes. For example, some embodiments may include a process for chemical synthesis having the steps of: compressing gaseous starting materials to an operating pressure of at least 200 bar, supplying the starting materials to a synthesis reactor (11), removing from the synthesis reactor (11) a product mixture which is liquid, and withdrawing mechanical energy from the product mixture by pressure reduction and using the energy in the step of compressing the starting materials.

In some embodiments, the product mixture is at least partly transferred into the gaseous phase before the step of withdrawing energy.

In some embodiments, the compressing step uses a piston type compressor (12) wherein to at least partly gaseous parts of the product mixture are introduced for withdrawing the energy.

In some embodiments, the step of withdrawing the energy from the at least partly gaseous product mixture uses a turbine apparatus (22), while at least parts of the product mixture are routed through the turbine apparatus (22) for withdrawing the energy.

In some embodiments, a generator connected to the turbine apparatus (22) is used for generating electric energy and at least some of the electric energy is used for the compressing step.

In some embodiments, a compressor mechanically directly connected to the turbine apparatus (22) via a shaft is used for the compressing step.

In some embodiments, to at least partly transfer the product mixture into the gaseous phase, the product mixture is expanded to lower pressure in a valve (15) and before, during and/or after said expansion, heat is withdrawn from the synthesis reactor (11) and supplied to the product mixture.

In some embodiments, to withdraw the energy from the at least partly gaseous product mixture, two or more turbine apparatuses (22, 31) are traversed.

In some embodiments, before traversing each of the turbine apparatuses (22, 31), the product mixture has heat supplied to it out of the synthesis reactor (11).

In some embodiments, the starting materials used are hydrogen and a carbonaceous gas and the product mixture comprises methanol and water.

As another example, some embodiments may include an apparatus (10) for chemical synthesis with: a facility (12) for compressing starting materials to an operating pressure of at least 200 bar, a synthesis reactor (11), means for supplying the starting materials to the synthesis reactor (11), means for removing from the synthesis reactor (11) a product mixture which is liquid, and a facility for withdrawing mechanical energy from the product mixture and transmitting the energy to the facility (12) for compression.

BRIEF DESCRIPTION OF THE DRAWINGS

Further advantageous elaborations will become apparent from the following description. In the drawings.

DETAILED DESCRIPTION

Figure 1:
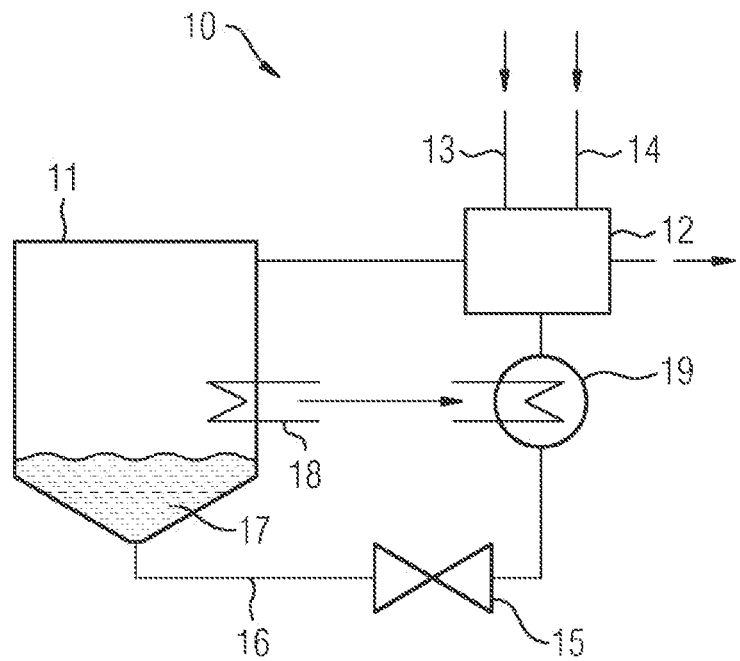
FIG. 1 shows in schematized form an apparatus for methanol synthesis using a piston-type compressor, according to teachings of the present disclosure.

The teachings of the present disclosure may include a synthesis process wherein gaseous starting materials are compressed and brought to an operating pressure of at least 200 bar, especially between 250 bar and 500 bar. The starting materials react in the synthesis reactor to form a product mixture which is at least largely liquid in the synthesis reactor. The product mixture, which typically also contains small admixtures of the starting materials in dissolved form, is removed from the synthesis reactor. The product mixture further has mechanical energy withdrawn from it by pressure reduction. This energy is used for compressing the starting materials.

The corresponding apparatus for chemical synthesis may comprise a facility for compressing starting materials to an operating pressure of at least 200 bar. The apparatus further comprises a synthesis reactor, means for supplying the starting materials to the synthesis reactor and means for removing from the synthesis reactor a product mixture which is liquid. The apparatus lastly comprises a facility for withdrawing mechanical energy from the product mixture and transmitting the energy to the facility for compression.

The synthesis processes and the apparati described herein may reduce the energy that needs to be supplied from the outside. The reason is that at least some of the energy necessary to compress the starting materials to the required pressure is withdrawn from the product mixture. The fact that the initial pressure of the starting materials is high is advantageous for this, since a lot of mechanical energy is then withdrawable from the liquid product mixture.

In this case, the various embodiments described are combinable with the features of any other or preferably also with those from two or more embodiments described. Accordingly, features yet additionally providable are as follows:

The product mixture is at least partly transferred into the gaseous phase before the step of withdrawing energy.

The facility for withdrawing the energy may be, for example, a turbine, a screw-type expander or a piston-type expander.

The compressing step may use a piston type compressor wherein to gaseous parts of the product mixture as drive gas are introduced for withdrawing the energy. Here the product mixture advantageously drives the compressing step directly without diversion via an interconnected form of energy such as, for example, electric energy.

The step of withdrawing the energy from the at least partly gaseous product mixture may also use a turbine apparatus. Here, gaseous parts of the product mixture are routed through the turbine apparatus for withdrawing the energy and thus provide kinetic energy. The kinetic energy, can then be used to generate electric energy using a generator mechanically connected to the turbine apparatus. At least some of the electric energy is then used for the compressing step. The advantage here is that the electric energy can be used for many purposes.

The turbine apparatus can be mechanically directly connected to a compressor via a shaft, which compressor is used for compressing the starting materials. Here the compressing step likewise works without diversions via electric energy.

To at least partly transfer the product mixture into the gaseous phase, the product mixture can be expanded to lower pressure in a valve. Further, before, during and/or after said expansion, heat can be withdrawn from the synthesis reactor or from the product mixture itself, at an upstream point, and supplied to the product mixture.

The step of withdrawing the energy from the at least partly gaseous product mixture may also be affected in two or more stages. In this case, two or more turbine apparatuses are traversed following removal of the product mixture. Here before traversing each of the turbine apparatuses, the product mixture can have heat supplied to it out of the synthesis reactor, to raise the gaseous fraction of the product mixture and/or achieve some superheating.

The process is particularly suitable for a methanol synthesis where a carbonaceous gas, especially carbon dioxide, and hydrogen are used as starting materials. The starting materials react in the synthesis reactor in accordance with reaction formula 1 to some extent to form methanol and water.

FIG. 1 shows a first example apparatus 10 for methanol generation according to teachings of the present disclosure. The apparatus 10 is supplied with starting materials in the form of carbon dioxide 13 and hydrogen 14. Said hydrogen 14 comes from an electrolysis apparatus in the present example. Water may be split into hydrogen and oxygen in the electrolysis apparatus not depicted in FIG. 1. Electricity from renewable energies may be used along with surplus electricity as produced when a large offering of renewable energies exceeds a simultaneous low demand for electricity.

The starting materials are fed to a piston-type compressor 12 in the first step. The piston-type compressor 12 compresses the starting materials to an operating pressure of 300 bar. It is under this pressure that the starting materials are fed, by a feedline, into the synthesis reactor 11. Inside the synthesis reactor 11 is where the conversion into methanol and water as per the reaction formula 1, mentioned at the outset, takes place. While the starting materials remain gaseous at the operating pressure of 300 bar, the products methanol and water are liquid at this pressure and the employed temperatures of 200° C. to 300° C. They therefore collect into a collection zone 17 and are removable from there out of the synthesis reactor 11. The precise form of reaction management within the synthesis reactor 11 may take on various forms and may include any appropriate systems or methods.

The product mixture of methanol, water, by-products, and admixtures of the starting materials is led in a removal line 16 to a valve 15 where the product mixture is expanded to a lower pressure of, for example, 100 bar. Here, depending on the remaining temperature and pressure, the product mixture may quickly become partly gaseous downstream of the valve 15. A heat exchanger 18 in the synthesis reactor 11 and a heat exchanger 19 coupled thereto are used to withdraw heat from the synthesis reactor 11 and supply it to the product mixture downstream of the valve 15, rendering a further portion of the product mixture gaseous. The gaseous portion of the product mixture is then supplied to the piston-type compressor 12 and there drives the step of compressing the starting materials. In effect, the pressurized product mixture serves as driving medium for compressing the starting materials via a mechanical piston-type system. Subsequently, the product mixture is sent for further working-up.

The heat exchanger 18 in the synthesis reactor 11 may be embodied as, for example, part of the cooling set-up, not depicted, for the synthesis reactor 11. The cooling set-up is used to maintain the temperature in the synthesis reactor 11 in the desired range as the exothermic reaction of reaction formula 1 proceeds. Since heat is removed in any case, this heat may be used to supply heat to the product mixture and thus transfer major proportions into the gaseous phase.

Multiple advantages are realized in the manner described: first, the methanol synthesis may be carried out at an operating pressure that allows the products to become liquid. As a result, the reaction products of reaction formula 1 may be constantly withdrawn from the reaction, causing the position of the equilibrium to shift substantially in the direction of the products. As a result, the reaction products do not have to be passed through the synthesis reactor 11 more than once for a good conversion to be attained. The increased investment of energy to provide the starting materials at the operating pressure of 300 bar is in turn earned back by making use of the energy of the product mixture, which is likewise under the high operating pressure. At the same time, the rejected heat of the synthesis reaction is also made advantageous use of by supplying it to the product mixture.

Figure 2:
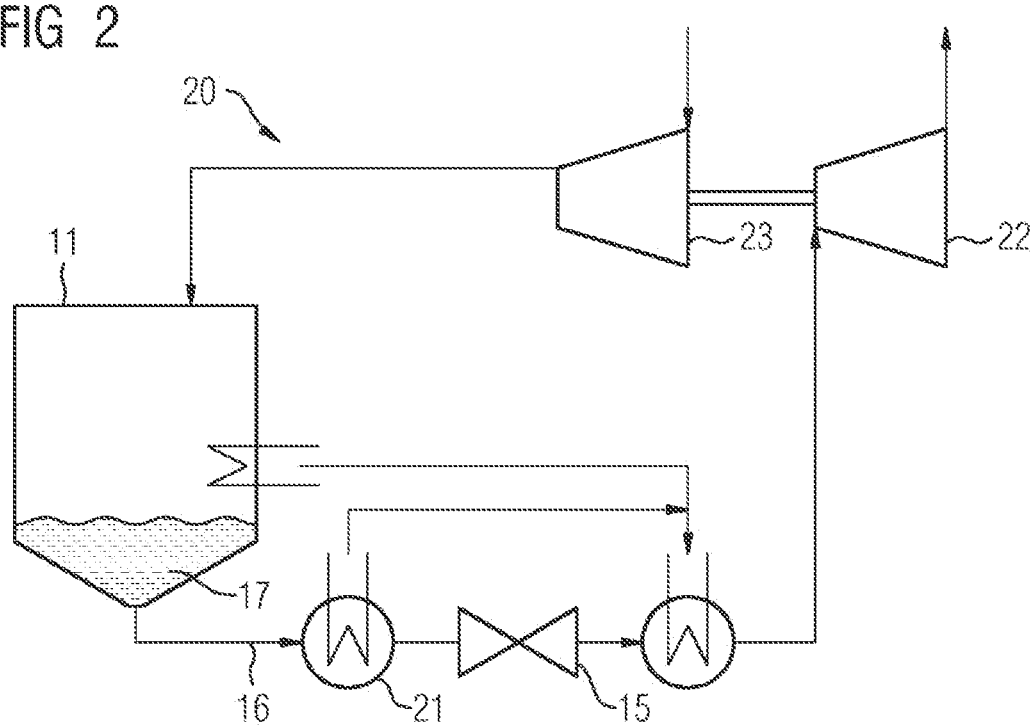
FIG. 2 shows in schematized form an apparatus for methanol synthesis using a turbine apparatus, according to teachings of the present disclosure.

A further working example is depicted in FIG. 2. The apparatus 20 of FIG. 2 corresponds in parts in this case to the apparatus 10 of the first working example. In contradistinction to the apparatus 10, however, the apparatus 20 of the second working example includes a further heat exchanger 21, located in the removal line 16 upstream of the valve 15. Said heat exchanger 21 withdraws heat from the product mixture and resupplies it in the heat exchanger 19 downstream of the valve 15.

The product mixture in this working example may be further supplied to a turbine apparatus 22 to drive the step of compressing the starting materials. The turbine apparatus 22 may be directly coupled mechanically via a shaft to a compressor 23, which compresses the starting materials to the working pressure. In some embodiments, the turbine apparatus 22 may be concurrently also used to generate electricity by additionally connecting it to a generator, which, however, is not shown in FIG. 2. The generator may also be embodied as an engine or motor and hence additionally provide electric energy from an external source for compression purposes.

Figure 3:
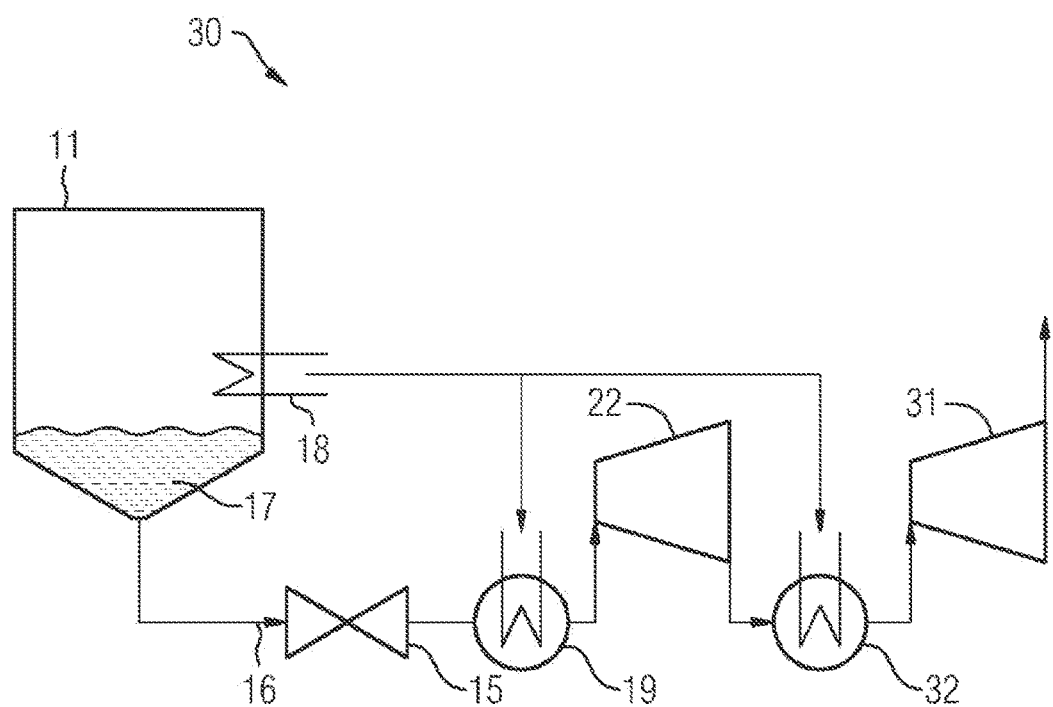
FIG. 3 shows in schematized form an apparatus for methanol synthesis using a multi-stage process for electricity generation, according to teachings of the present disclosure.

Since the product mixture is under an appreciable operating pressure, the exploitation of the energy may be further improved by using a multi-stage process. A corresponding apparatus 30 according to a third working example of the invention is depicted in FIG. 3. The apparatus 30, like the above-described apparatuses 10 and 20, contains a synthesis reactor 11 having a collection region 17 and a heat exchanger 18 at the synthesis reactor 11.

The step of supplying the starting materials to the synthesis reactor 11 is not shown in the apparatus 30 of the third working example. Here, in a manner similar to that for the second apparatus 20, the product mixture is supplied to a turbine apparatus 22 while upstream thereof heat from the synthesis reactor 11 is supplied by means of the heat exchanger 19. After passage through the turbine apparatus 22, however, and in contradistinction to the above-described apparatuses 10 and 20, the product mixture may be supplied to a further turbine apparatus 31 and before entry into the further turbine apparatus 31, the product mixture is supplied with further heat from the synthesis reactor 11 by means of a further heat exchanger 32.

The two-stage process here may also be extended to more than two stages. The turbine apparatuses 22 and 31 therein feed, directly or indirectly, as already described, the step of compressing the starting materials and expediently also, for example, a generator for generation of electric energy. The step of compressing the starting materials may also be affected in two or more stages.

In a simplified embodiment, operation is also possible without the valve 15. In this case, the product mixture is not transferred into the gaseous phase but is instead supplied directly in liquid form to an engine such as, for example, a turbine. Partial vaporization of the products in the product mixture may occur in the engine owing to the high temperature of the product mixture. This may be tolerated; alternatively, however, the product mixture may also be cooled with an interconnected heat exchanger before being routed into the engine.

What is claimed is:

1. A method for chemical synthesis, the method comprising:
   compressing gaseous starting materials to an operating pressure of at least 200 bar;
   supplying the starting materials to a synthesis reactor;
   removing a product mixture from the synthesis reactor in a liquid state;
   at least partially converting the product mixture into a gaseous phase;
   withdrawing mechanical energy from the at least partially gaseous product mixture by reducing a pressure of the product mixture; and
   using the mechanical energy to compress the gaseous starting materials.

2. The method as claimed in claim 1, wherein compressing the gaseous starting materials includes using a piston type compressor.

3. The method as claimed in claim 1, wherein withdrawing mechanical energy from the at least partly gaseous product mixture includes using a turbine apparatus and at least part of the product mixture is routed through the turbine apparatus for withdrawing the energy.

4. The method as claimed in claim 3, further comprising using a generator connected to the turbine apparatus for generating electric energy and at least some of the electric energy is used for the compressing step.

5. The method as claimed in claim 3, further comprising using a compressor mechanically directly connected to the turbine apparatus via a shaft for compressing the gaseous starting materials.

6. The method as claimed in claim 1, wherein at least partly converting the product mixture into the gaseous phase includes expanding the product mixture to a lower pressure in a valve withdrawing heat from the synthesis reactor to supply the heat to the product mixture.

7. The method as claimed in claim 1, further comprising engaging two or more turbine apparati to withdraw the mechanical energy from the product mixture.

8. The method as claimed in claim 3, further comprising supplying heat out of the synthesis reactor to the product mixture before it traverses a turbine apparatus.

9. The method as claimed in claim 1, wherein the product mixture includes methanol and the starting materials comprises hydrogen and a carbonaceous gas.

* * * * *